(12) United States Patent
Petrick et al.

(10) Patent No.: US 7,901,425 B2
(45) Date of Patent: Mar. 8, 2011

(54) ILIAC BIFURCATION BALLOON CATHETER

(75) Inventors: Timothy Petrick, Brooklyn Park, MN (US); Steven Willard, Brooklyn Center, MN (US)

(73) Assignee: Cordis Corporation, Miami Lakes, FL (US)

( * ) Notice: Subject to any disclaimer, the term of this patent is extended or adjusted under 35 U.S.C. 154(b) by 983 days.

(21) Appl. No.: 10/379,911

(22) Filed: Mar. 6, 2003

(65) Prior Publication Data
US 2003/0220664 A1 Nov. 27, 2003

Related U.S. Application Data

(60) Provisional application No. 60/362,576, filed on Mar. 7, 2002.

(51) Int. Cl.
*A61M 29/00* (2006.01)
*A61M 25/00* (2006.01)
(52) U.S. Cl. .................................. 606/194; 604/528
(58) Field of Classification Search .......... 606/192–194; 623/1.11; 604/523, 528, 532, 103.05; 600/585
See application file for complete search history.

(56) References Cited

U.S. PATENT DOCUMENTS

| | | | | |
|---|---|---|---|---|
| 4,582,181 A | * | 4/1986 | Samson | 606/194 |
| 4,774,949 A | * | 10/1988 | Fogarty | 606/108 |
| 4,811,743 A | * | 3/1989 | Stevens | 600/585 |
| 4,976,691 A | * | 12/1990 | Sahota | 604/103.05 |
| 6,022,342 A | * | 2/2000 | Mukherjee | 604/523 |
| 6,224,609 B1 | | 5/2001 | Ressemann et al. | |
| 6,261,316 B1 | | 7/2001 | Shaolian | |
| 6,514,262 B1 | * | 2/2003 | Di Fiore et al. | 606/131 |

FOREIGN PATENT DOCUMENTS

| | | |
|---|---|---|
| EP | 0684022 B1 | 2/2004 |
| WO | WO 99/44539 A2 | 9/1999 |

OTHER PUBLICATIONS

International Search Report for corresponding application No. PCT/US03/06631.

* cited by examiner

*Primary Examiner* — Julian W Woo

(57) ABSTRACT

A balloon catheter may be used to access side branch arteries such as the iliac artery. The catheter includes a guidewire configured to carry a balloon and deploy directly in a branch leg without traversing acute bends.

6 Claims, 6 Drawing Sheets

ILIAC BIFURCATION BALLOON CATHETER

This application claims the benefit of U.S. Provisional Application No. 60/362,576 filed Mar. 7, 2002, which is hereby incorporated by reference.

I. BACKGROUND OF THE INVENTION

1. Field of the Invention

The present invention relates to devices and methods for repairing aneurysms, and more particularly, to a balloon catheter operable to position a balloon in a branch artery from an ipsilateral access site.

2. Discussion of the Related Art

An aneurysm is an abnormal dilation of a layer or layers of an arterial wall, usually caused by a systemic collagen synthetic or structural defect. An abdominal aortic aneurysm is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

Aneurysms may be classified or typed by their position as well as by the number of aneurysms in a cluster. Typically, abdominal aortic aneurysms may be classified into five types. A Type I aneurysm is a single dilation located between the renal arteries and the iliac arteries. Typically, in a Type I aneurysm, the aorta is healthy between the renal arteries and the aneurysm and between the aneurysm and the iliac arteries.

A Type II A aneurysm is a single dilation located between the renal arteries and the iliac arteries. In a Type II A aneurysm, the aorta is healthy between the renal arteries and the aneurysm, but not healthy between the aneurysm and the iliac arteries. In other words, the dilation extends to the aortic bifurcation. A Type II B aneurysm comprises three dilations. One dilation is located between the renal arteries and the iliac arteries. Like a Type II A aneurysm, the aorta is healthy between the aneurysm and the renal arteries, but not healthy between the aneurysm and the iliac arteries. The other two dilations are located in the iliac arteries between the aortic bifurcation and the bifurcations between the external iliacs and the internal iliacs. The iliac arteries are healthy between the iliac bifurcation and the aneurysms. A Type II C aneurysm also comprises three dilations. However, in a Type II C aneurysm, the dilations in the iliac arteries extend to the iliac bifurcation.

A Type III aneurysm is a single dilation located between the renal arteries and the iliac arteries. In a Type III aneurysm, the aorta is not healthy between the renal arteries and the aneurysm. In other words, the dilation extends to the renal arteries.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via transperitoneal or retroperitoneal approach has been the standard treatment, it is associated with significant risk. For example, complications include perioperative myocardial ischemia, renal failure, erectile impotence, intestinal ischemia, infection, lower limb ischemia, spinal cord injury with paralysis, aorta-enteric fistula, and death. Surgical treatment of an abdominal aortic aneurysm is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital, and a convalescence period at home from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurysmal segment with a prosthetic device. This surgery, as described above, is a major undertaking, with associated high risks and with significant mortality and morbidity.

Over the past five years, there has been a great deal of research directed to developing less invasive, percutaneous, e.g., catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now FDA approved and commercially available. The delivery procedure typically involves advanced angiographic techniques performed through vascular accesses gained via surgical cutdown of a remote artery, such as the common femoral or brachial arteries. Over a guidewire, the appropriate size introducer will be placed. The catheter and guidewire is passed through the aneurysm, and with the appropriate size introducer housing a stent-graft, the stent-graft will be advanced along the guidewire to the appropriate position. Typical deployment of the stent-graft device requires withdrawal of an outer sheath while maintaining the position of the stent-graft with an inner-stabilizing device. Most stent-grafts are self-expanding; however, an additional angioplasty procedure, e.g., balloon angioplasty, may be required to secure the position of the stent-graft. Following the placement of the stent-graft, standard angiographic views may be obtained.

Due to the large diameter of the above-described devices, typically greater than twenty French (3F=1 mm), arteriotomy closure requires surgical repair. Some procedures may require additional surgical techniques, such as hypogastric artery embolization, vessel ligation, or surgical bypass in order to adequately treat the aneurysm or to maintain flow to both lower extremities. Likewise, some procedures will require additional, advanced catheter directed techniques, such as angioplasty, stent placement, and embolization, in order to successfully exclude the aneurysm and efficiently manage leaks.

While the above-described endoprostheses represent a significant improvement over conventional surgical techniques, there is a need to improve the endoprostheses, their method of use and their applicability to varied biological conditions. Accordingly, in order to provide a safe and effective alternate means for treating aneurysms, including abdominal aortic aneurysms and thoracic aortic aneurysms, a number of difficulties associated with currently known endoprostheses and their delivery systems must be overcome. One concern with the use of endoprostheses is the prevention of endo-leaks and the disruption of the normal fluid dynamics of the vasculature.

Devices using any technology should preferably be simple to position and reposition as necessary, should preferably provide an acute fluid tight seal, and should preferably be anchored to prevent migration without interfering with normal blood flow in both the aneurysmal vessel as well as branching vessels. In addition, devices using the technology should preferably be able to be anchored, sealed, and maintained in bifurcated vessels, tortuous vessels, highly angulated vessels, partially diseased vessels, calcified vessels, odd shaped vessels, short vessels, and long vessels. In order to accomplish this, the endoprostheses should preferably be extendable and reconfigurable while maintaining acute and long term fluid tight seals and anchoring positions.

The endoprostheses should also preferably be able to be delivered percutaneously utilizing catheters, guidewires and other devices which substantially eliminate the need for open surgical intervention. Accordingly, the diameter of the endoprostheses in the catheter is an important factor. This is especially true for aneurysms in the larger vessels, such as the thoracic aorta.

Another concern associated with devices and methods for repairing aneurysms is graft in-folding in smaller vessels. For example, a particular endoprosthesis may have a branch extending into an internal iliac artery. A graft in-fold in a smaller vessel, such as an internal iliac, may create blood flow disruptions that narrow the lumen. Accordingly, ballooning the side arm endoprosthesis irons the fabric folds and expands the stents to fully oppose the vessel wall. Therefore, a balloon catheter which is capable of delivering a balloon in a branch vessel, such as an internal iliac, from an ipsilateral access site is needed.

III. SUMMARY OF THE INVENTION

The iliac bifurcation balloon catheter of the present invention overcomes the limitations of the devices and methods as briefly described above.

The iliac bifurcation balloon catheter comprises an inflation lumen that makes a one-hundred eighty degree turnabout with an independently steerable guidewire/balloon combination enclosed in an external sheath with through wire capacity, an atraumatic tip and the ability to launch/steer/inflate/deflate/recapture the balloon in a retro direction.

The iliac bifurication balloon catheter guidewire transitions from an atraumatic tip to a kink resistant stiffness in approximately five centimeters. The balloon catheter is operable to access acutely angulated side branches from an ipsilateral cutdown and may be utilized to apply reasonably significant force to cross tight lesions in side-branch arteries.

The iliac bifurcation balloon catheter may be utilized to access other side branch arteries and to perform other functions. For example, the catheter may be longer for accessing the renal arteries. The catheter may be designed with a longer or shorter retro extension with varying size diameters, with high pressure balloons, with conforming balloons and with different balloon sizes. The iliac bifurcation balloon catheter may be configured and used as a delivery/expansion system for other devices, e.g., stents, embolizing coils, occluding devices, drugs and sensors. In addition, the balloon catheter may be used to assist in determining side branch location and/or angle as well as for a diagnostic or contrast media injection port.

IV. BRIEF DESCRIPTION OF THE DRAWINGS

V. DETAILED DESCRIPTION OF THE PREFERRED EMBODIMENTS

The iliac bifurcation (IB) balloon catheter of the present invention may be employed as an accessory device to the Tributary™ Stent Graft System disclosed in U.S. Pat. No. 6,224,609 and incorporated by reference herein. The IB balloon catheter may be utilized to facilitate post-ballooning of the side-arm 15 of a bifurcated endovascular prosthesis 10 illustrated in FIG. 1, as necessary per the discretion of the physician. Animal studies and clinical studies have demonstrated that post-ballooning prosthesis side-arms, may be desired in some cases. One of the primary functions of the catheter system of the present inveniton is to position a balloon within a prosthesis side-arm from an ipsilateral access site.

Since the internal iliac artery is a relatively small vessel (approximately 5-8 mm), graft in-folding may create flow disruptions that narrow the lumen. Ballooning the side-arm prosthesis "irons" the fabric folds and expands the stents to fully oppose the vessel wall.

Figure 2A:
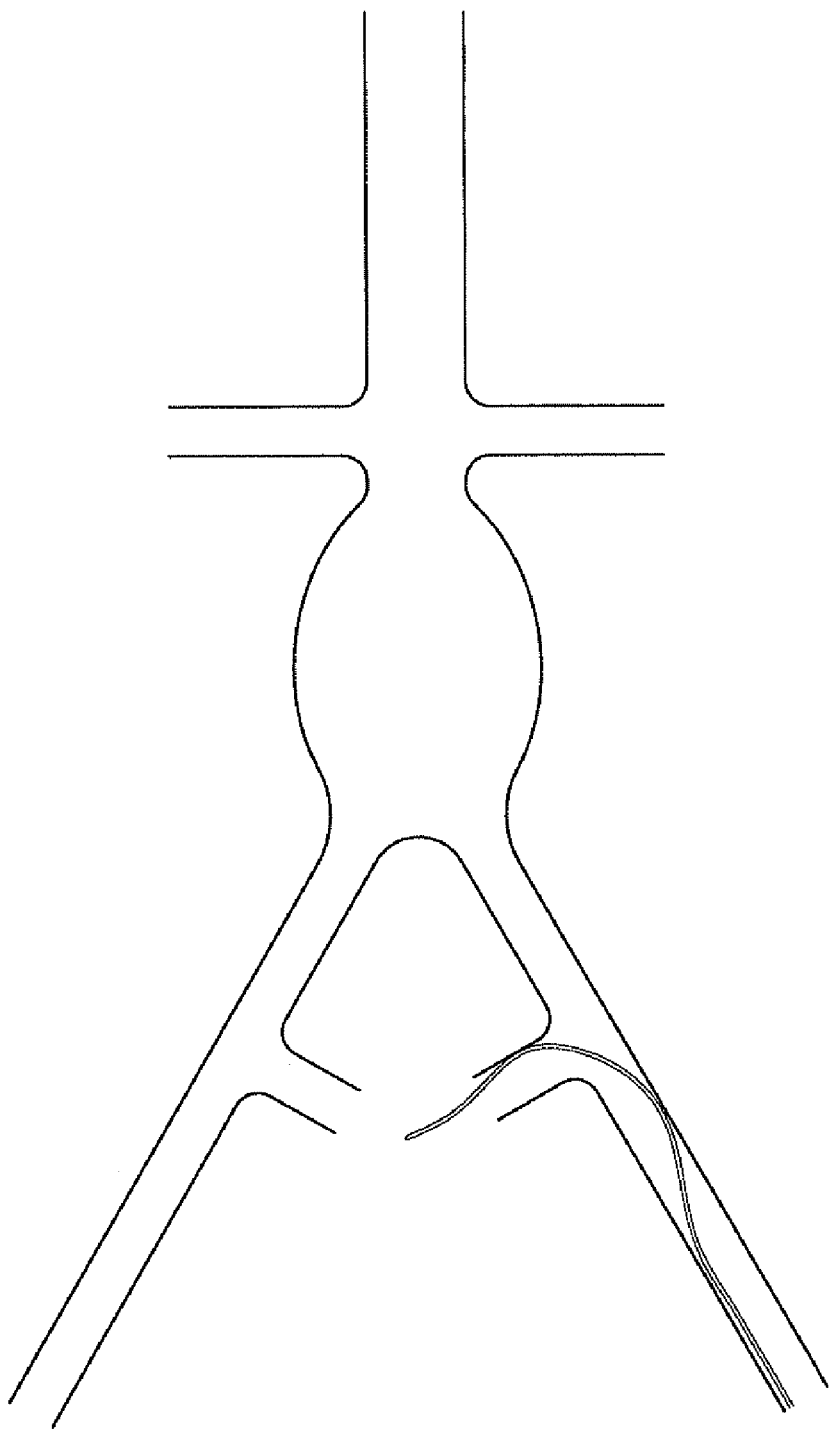
FIG. 2a illustrates an ipsilateral insertion procedure for a catheter.
Figure 2B:
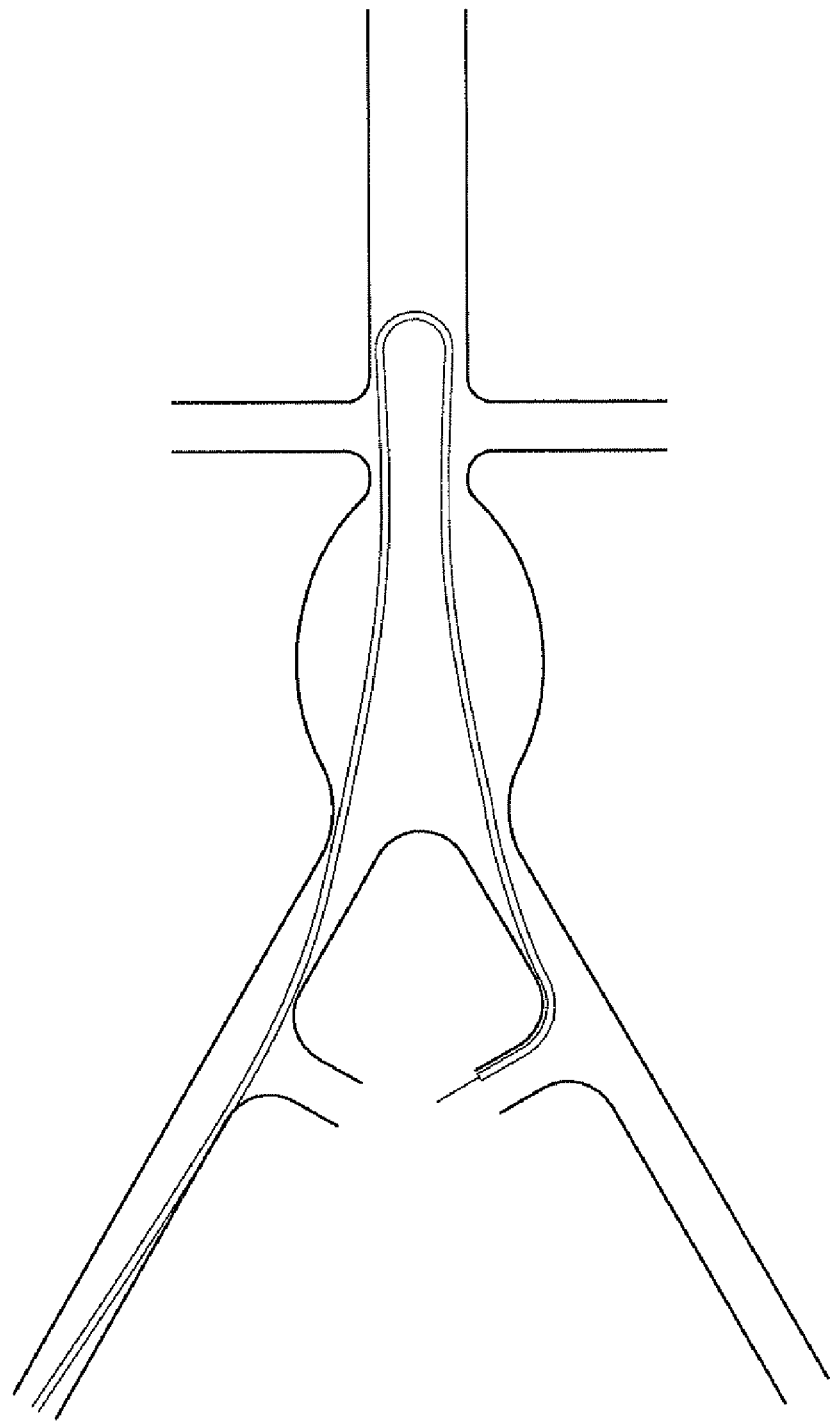
FIG. 2b shows a contralateral insertion procedure for a catheter.

Accessing the internal iliac artery after implantation of the bifurcated prosthesis is difficult using currently marketed balloon catheters. FIGS. 2a and 2b show an ipsilateral and contralateral approach, respectively, for positioning a balloon catheter in the internal iliac artery using currently marketed balloon catheters. (For clarity, the prostheses are not included in FIGS. 2a and 2b.)

Using an ipsilateral approach the balloon catheter must traverse an acute bend and track back against the direction it is being advanced (FIG. 2a). Removing the ipsilaterally positioned balloon is also difficult because the balloon must track around the acute bend without snagging on the ends of the stents in the prostheses.

Using a contralateral approach (FIG. 2b) the catheter must track through a bifurcated prosthesis such as the Ariba™ prosthesis developed by Teramed Corporation. The catheter would traverse up one prosthesis leg, over the bifurcation, and down the opposite prosthesis leg to access the internal iliac side-arm 15. Potential risks while removing the balloon catheter include catching on stents and/or dislodging the bifurcated prosthesis.

Figure 3:
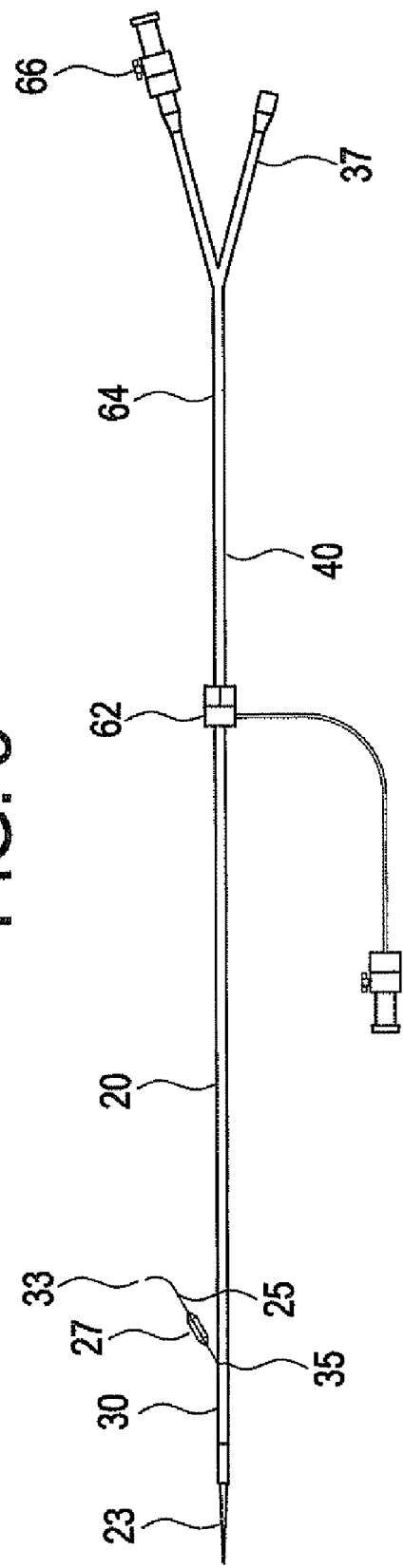
FIG. 3 depicts an iliac bifurcation balloon catheter according to the invention.

In keeping with the present invention, as illustrated in FIG. 3, the balloon catheter system of the present invention includes a sheath 20 having a tip 23 disposed at one end and an internal iliac guidewire 25 attached to a balloon 27 to facilitate accessing the internal iliac artery. The IB catheter is further provided with a sheath marker 60, a hemostasis valve 62 and a proximal stop 64.

Figure 4:
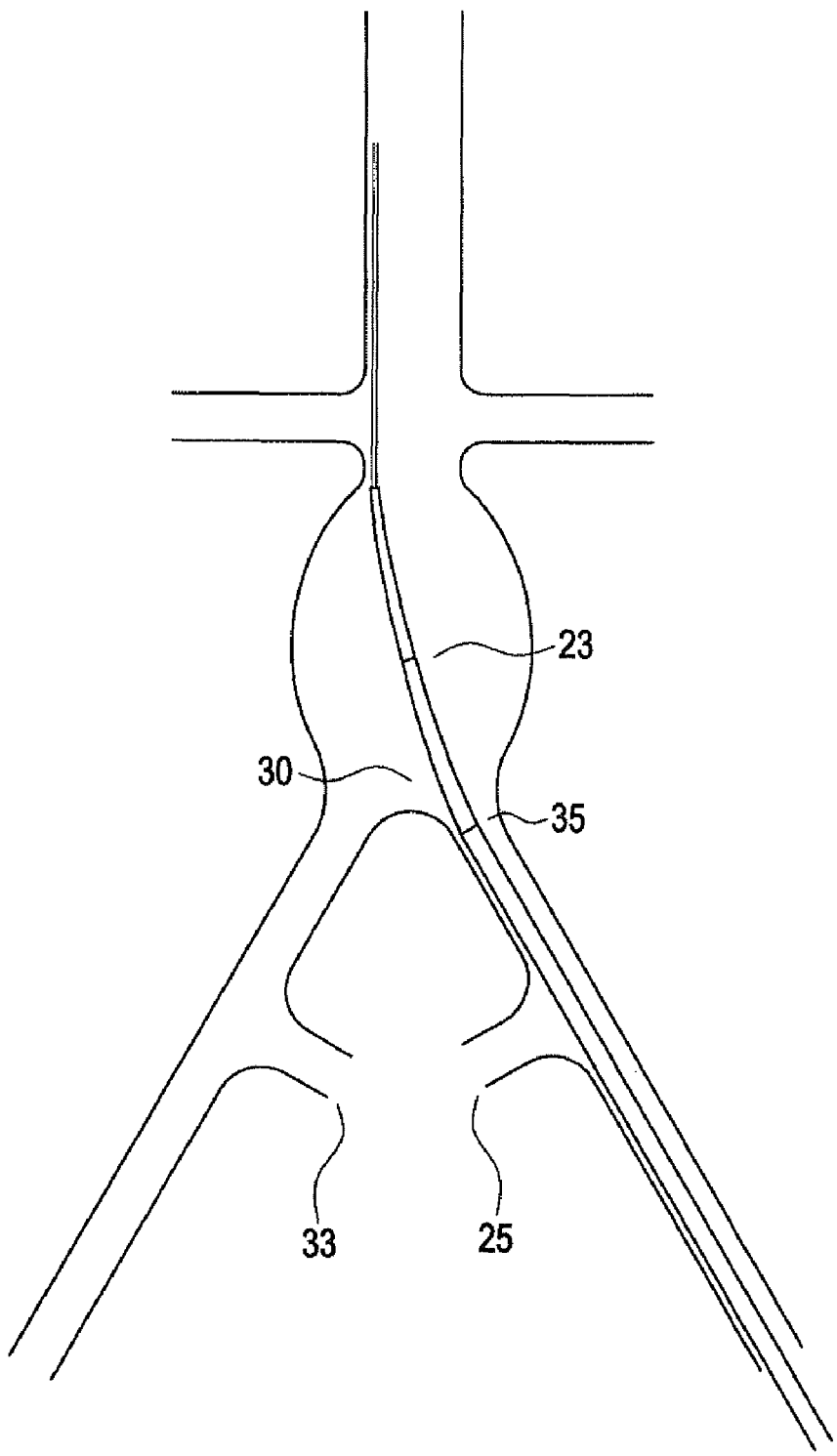
FIG. 4 illustrates an iliac bifurcation balloon catheter deployed in an arterial system.

The IB balloon catheter of the present invention improves the post-ballooning procedure by simplifying the ipsilateral approach. Internal or "retrograde" guidewire 25 accesses the internal iliac artery from a favorable angle and eliminates tracking around an acute bend (FIG. 4).

The IB balloon catheter system preferably utilizes the "retrograde" wiring technology developed for the delivery system described in U.S. Pat. No. 6,224,609. In the exemplary embodiment, a 2 cm×8 mm balloon 27 follows guidewire 25 as it tracks through sheath port 30 and into a side-branch vessel 15. Preferably, radiopaque markers indicate the location of sheath port 30 and the working length of balloon 27.

Figure 5:
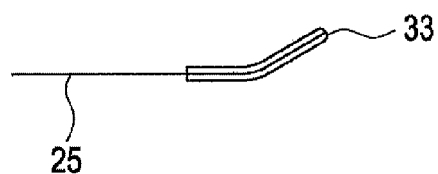
FIG. 5 illustrates an iliac guidewire in accordance with the invention.

In keeping with the invention, guidewire 25 preferably exhibits a rapid transition to an atraumatic tip 33 as best illustrated in FIG. 5. The rapid transition minimizes the length of wire extended into the hypogastric artery during balloon placement. Because of this rapid transition, the wire tip stiffness is comparable to a 0.035 "J" type guidewire even though the core wire diameter is preferably about 0.018 inches.

Guidewire 25 preferably has sufficient strength and kink resistance to track the balloon into the internal iliac artery. This wire stiffness transition may be attained by tapering the wire from 0.004" diameter at tip 33 to 0.018" diameter over a 5 cm length. A heat set bend is preferably provided at tip 33 of guidewire 25 to allow guidewire 25 to track out of sheath port 30. The heat set bend also predisposes guidewire 25 toward the internal iliac artery.

As illustrated in FIG. 5, the heat set bend preferably subtends an angle of between 60° and 70°. More preferably, the heat set bend subtends an angle of about 65°. Tip 33 preferably includes a radiopaque marker, e.g., a platinum coil.

Figure 6:
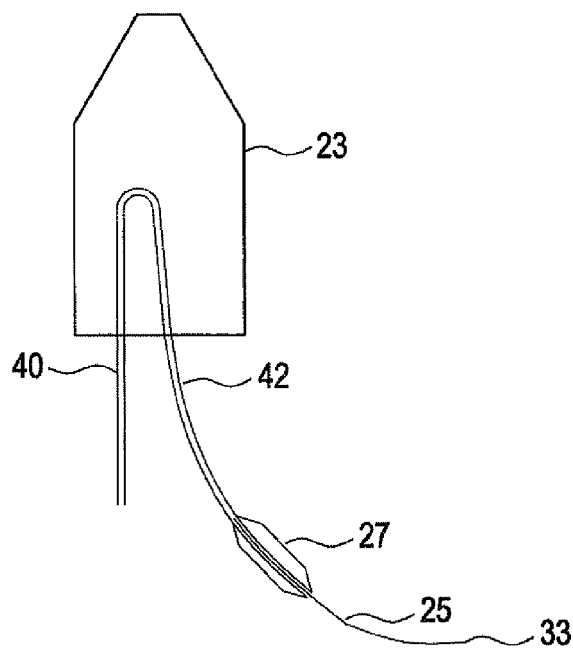
FIG. 6 shows a distal manifold in accordance with the invention.

As illustrated in FIG. 6, guidewire 25 is preferably heat bonded to the end of the balloon shaft. Guidewire 25 may extend through balloon 27 as far as the junction of balloon shaft 42 and the catheter extension 40. The catheter extension 40 may be manipulated to steer and extend guidewire 25 out of sheath port 30 and into the internal iliac artery.

Balloon 27 is preferably heat bonded to the balloon shaft 42. Balloon 27 preferably has a 2 cm working length and an 8 mm diameter. The balloon is designed for the low pressure application of "ironing" fabric folds out of the side-arm of bifurcated prostheses. The intended working pressure is about three atmospheres. The working length may be marked by first and second radiopaque markers, e.g., platinum bands, swaged to the balloon shaft.

The catheter preferably has a central guidewire lumen 37 (FIG. 3) compatible with a 0.035 inch guidewire for advancement of the catheter into the body. An atraumatic tapered tip 23 may be incorporated at the catheter leading edge. Tapered tip 23 provides flexibility at the leading edge of the catheter and provides a seal at the sheath end to protect sheath 20 from "catching" during catheter advancement.

Catheter tip 23 is preferably heat bonded to the balloon shaft 42 and catheter extension 40 to form a distal balloon manifold as illustrated in FIG. 6. The distal manifold heat bond creates a geometry that allows the catheter to effectively "double-back" on itself. For example, catheter extension 40 and balloon shaft 42 form a substantially U-shaped bend of about 180° at or near the heat bond.

Figure 7:
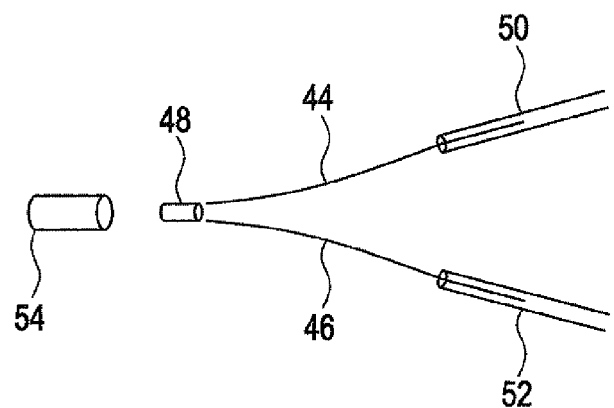
FIG. 7 depicts components used in forming a heat bond between first and second lumens and a catheter tip in accordance with the invention.

In accordance with an aspect of the invention, the distal manifold may be formed by fusing catheter extension 40 and balloon shaft 42 in tip 23. As depicted in FIG. 7, in the construction process, a pair of wire mandrels 44 and 46 may be snuggly inserted into a non-melting thin wall tube 48. First and second plastic tubes 50 and 52, respectively, may be slid onto wire mandrels 44 and 46 to within about 0.25" of non-melting tube 48. First and second tubes may comprise, e.g., balloon shaft 42 and catheter extension 40. A heat shrinkable tube 54 may be slid onto the assembly over the non-melting tube 48 to about 1/16" past the ends of first and second tubes 50 and 52. The assembly may then be heated until the protruding tips of first and second tubes 50 and 52 begin to melt. While continuing to heat, wire mandrels 44 and 46 may be gently drawn until non-melting tube 48 sinks into the melted portions of tubes 50 and 52 and approximately 1/16" into heat shrinkable tube 54. Heating should be continued until molten plastic flows back around non-melting tube 48 and the tips of wire mandrels 44 and 46. The assembly may then be cooled and the wire mandrels removed. Thereafter the assembly may be heat bonded to catheter tip 23.

In accordance with the invention, other methods of constructing the distal manifold are within the purview of the skilled artisan in view of the foregoing disclosure.

In the finished system, catheter extension 40 and the "doubled-back" balloon shaft 42 are enclosed within sheath 20. Sheath 20 has a side port that allows the guidewire and balloon to be tracked out of sheath 20 and then recaptured within sheath 20 by manipulating catheter extension 40. The sheath port is preferably marked with a platinum band for radiopacity.

Figure 1:
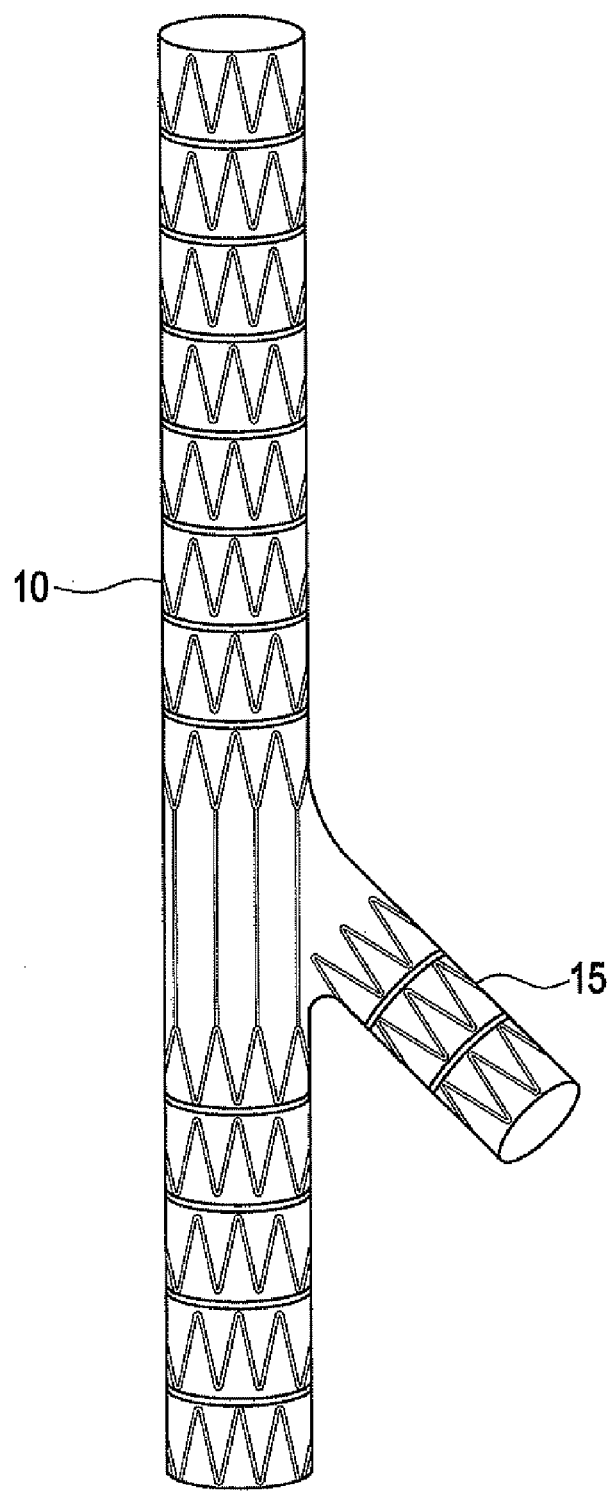
FIG. 1 depicts a bifurcated prosthesis.

As mentioned above, the IB catheter of the present invention may be used to address graft in-folding and open the side-arm of a bifurcated prothesis. To perform that operation, the IB balloon catheter of the present invention may be advanced over a catheter guidewire until a sheath marker 60 is positioned at the bifurcation of the prosthesis (FIG. 1). Sheath 20 is preferably held stationary as catheter extension 40 is advanced through hemostasis valve 62 to the level of proximal stop 64. Catheter extension 40 may be rotated to steer guidewire 25 out of the sheath port 30. The catheter system may be rotated to align sheath port 30 with the ostium of the internal iliac artery.

While maintaining sheath position, catheter extension 40 may be retracted to advance guidewire 25 out of sheath port 30 into the deployed side-arm prosthesis. Retraction of catheter extension 40 is preferably continued until balloon 27 is appropriately positioned within the side-arm 15.

Balloon 27 may be inflated by connecting an inflation device to a balloon inflation port 66. Balloon 27 may be deflated and repositioned as required. After the desired result has been attained, i.e., the side-arm has been appropriately opened, balloon 27 may be deflated by pulling a vacuum and the balloon inflation port is closed.

While maintaining the position of sheath 20, catheter extension 40 may be advanced to withdraw balloon 27 and guidewire 25 from the artery into sheath 20. Catheter extension 40 may be rotated to capture guidewire tip 33, then retracted to reposition catheter tip 33 within sheath 20. The catheter may then be removed from the patient.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the paticular constructions described and illustrated, but should be construed to cohere with all modifications that may fall within the scope of the appended claims.

What is claimed is:

1. A balloon catheter for delivery of a balloon in a branch vessel from an ipsilateral access site comprising:

an external sheath having a single sheath port opening and a lumen extending therethrough, the external sheath being deliverable into a main artery, the sheath port opening being configured for access into an internal iliac artery;

an internal iliac guidewire, having a heat set, acute angle bend of about 65 degrees at an atraumatic tip attached to the internal iliac guidewire for passing through the sheath port opening and entry into an internal iliac artery, the atraumatic tip has a diameter that tapers from 0.004 inches to 0.018 inches over a linear distance of 5 cm, the sheath port opening configured to direct the internal iliac guidewire into an internal iliac artery with the external sheath remaining in a main artery, thereby facilitating an ipsilateral approach, the sheath port opening being proximal of a distal tip of the external sheath;

a moveable catheter extension for steering and extending the internal iliac guidewire out through the sheath port opening;

a catheter tip defining a manifold;

a balloon shaft joined to the internal iliac guidewire on one end and to the moveable catheter extension on the other end, the balloon shaft and the catheter extension being connected within the catheter tip and forming a U-shaped bend of about 180° within the manifold for directing the internal iliac guidewire through the sheath port opening, the catheter tip comprising a tapered structure for flexibility at its distal end and a seal at the sheath, the catheter extension and the balloon shaft being partially enclosed within the external sheath; and a balloon mounted on the balloon shaft proximate the atraumatic tip of the internal iliac guidewire, wherein the balloon shaft, the balloon, the internal iliac guidewire and the atraumatic tip extend in a proximal direction from the sheath port opening of the external sheath substantially parallel to the external sheath for ballooning an internal iliac artery.

2. The balloon catheter of claim 1 further comprising first and second radiopaque markers connected to the balloon shaft proximate to the ends of the balloon.

3. The balloon catheter of claim 1 wherein the catheter tip is heat bonded to the catheter extension and the balloon shaft.

4. The balloon catheter of claim 3 further comprising a non-melting tube heat bonded to the junction of the catheter extension and the balloon shaft.

5. The balloon catheter of claim 1 wherein the external sheath includes a radiopaque marker to indicate the location of the sheath port opening.

6. The balloon catheter of claim 1 wherein the guidewire has sufficient kink resistance to track the balloon through the sheath port opening.

* * * * *